United States Patent
Nakamura et al.

(10) Patent No.: US 6,511,437 B1
(45) Date of Patent: Jan. 28, 2003

(54) HEAD BLOOD FLOW BALANCE INSPECTING APPARATUS

(76) Inventors: Yoshinobu Nakamura, 18-3, Yoneyama 4-chome, Niigata-shi, Niigata-ken (JP); Kiyoharu Nakamura, 3295, Oaza-Nishidani, Koshiji-machi, Santo-gun, Niigata-ken (JP)

( * ) Notice: Subject to any disclaimer, the term of this patent is extended or adjusted under 35 U.S.C. 154(b) by 15 days.

(21) Appl. No.: 09/690,465

(22) Filed: Oct. 18, 2000

(30) Foreign Application Priority Data

Nov. 15, 1999 (JP) .......................................... 11-323786

(51) Int. Cl.⁷ ................................................ A61B 5/02
(52) U.S. Cl. ...................................... 600/504; 600/549
(58) Field of Search ................................ 600/473–475, 600/504, 549

(56) References Cited

U.S. PATENT DOCUMENTS

| 3,651,694 A | * | 3/1972 | Lamb ........................... 374/114 |
| 3,933,045 A | * | 1/1976 | Fox et al. .................... 374/134 |
| 4,297,685 A | * | 10/1981 | Brainard, II ................. 340/575 |
| 4,325,386 A | * | 4/1982 | Katz ............................ 600/546 |
| 5,017,018 A | * | 5/1991 | Iuchi et al. .................. 374/130 |
| 5,469,855 A | * | 11/1995 | Pompei et al. .............. 600/474 |
| 5,522,662 A | * | 6/1996 | Shiokawa ..................... 374/130 |
| 5,664,578 A | * | 9/1997 | Bozcán ........................ 600/549 |
| 6,325,763 B1 | * | 12/2001 | Pfeiffer et al. .............. 600/549 |

FOREIGN PATENT DOCUMENTS

| JP | 59-176940 | 11/1984 |
| JP | 60-25427 | 2/1985 |
| JP | 61-138130 | 6/1986 |
| JP | 11-113856 | 4/1999 |

* cited by examiner

*Primary Examiner*—Robert L. Nasser
*Assistant Examiner*—Patricia Mallari
(74) *Attorney, Agent, or Firm*—Connolly Bove Lodge & Hutz, LLP; Larry J. Hume

(57) ABSTRACT

To provide a head blood flow balance inspecting apparatus for preventing apoplexy or brain infarct, a head blood flow balance inspecting apparatus comprising two ear interior thermometric portions, a connecting portion for connecting the two ear interior thermometric portions and a display portion for displaying a measurement result of the two ear interior thermometric portions. The right and left ears interior temperatures of the person to be inspected are measured and the measurement result is displayed on the display portion to accurately detect right and left blood flow balance of the head portion.

10 Claims, 3 Drawing Sheets

HEAD BLOOD FLOW BALANCE INSPECTING APPARATUS

BACKGROUND OF THE INVENTION

The present invention relates to a head blood flow balance inspecting apparatus for preventing mainly apoplexy or brain infarct.

It is extensively known that brain infarct is liable to be induced when a feed amount of blood to a brain is reduced, and apoplexy is liable to be induced in the case where a blood pressure is high. These conditions of disease occur at a position where the blood flow condition in the brain is asymmetric. In any case, those diseases are more likely to occur in the case where the right and left blood flows in the head portion become unbalance in comparison to the case where the right and left blood flows in the head portion is well balanced.

Therefore, it is possible to take an approach to measure and compare body temperatures within right and left ears to know the presence/absence of the blood flow insufficiency as a simple inspection means of the blood flow conditions on the right and left of the head portion. However, since the conventional equipment (thermometer for measuring the interior of the ear) is provided only with a single ear interior thermometer portion, in the case the right and left ear temperatures are measured in order by using the same equipment, the ear interior temperatures on the right and left sides are not always measured under the same thermometric measurement condition due to the body temperature of the person to be measured by holding the equipment by the person. Namely, there is a fear that the precise measurement would not be performed.

SUMMARY OF THE INVENTION

In order to overcome the above-noted defects, an object of the present invention is provide a novel head blood flow balance inspecting apparatus for measuring accurately and simultaneously the right and left ear internal temperatures.

According to a first aspect of the present invention, there is provided a head blood flow balance inspecting apparatus comprising two ear interior thermometric portions, a connecting portion for connecting the two ear interior thermometric portions and a display portion for displaying a measurement result of the two ear interior thermometric portions.

In the head blood flow balance inspecting apparatus according to the first aspect of the invention, the connecting portion is used to connecting the two ear interior thermometric portions, the two ear interior thermometric portions are provided at tip end portions to face each other, and the connecting portion is formed by an elastic member for biasing the two ear interior thermometric portions in a direction to face each other.

Also, in the head blood flow balance inspecting apparatus according to the first aspect of the invention, each of the ear interior thermometric portions is composed of a sensor portion to be inserted into the ear and a body portion projecting with the sensor portion, the sensor portion being forced to convert the ear interior detected temperature detected by an infrared ray sensor into an electrical signal and to feed it to a display portion, and the body portion interrupts the communication between an external auditory meatus and an outside, the sensor portion is inserted into a ear hole at a suitable position and condition and is formed to be stable in that condition.

Also, in the head blood flow balance inspecting apparatus according to the second aspect of the invention, each of the ear interior thermometric portions is composed of a sensor portion to be inserted into the ear and a body portion projecting with the sensor portion, the sensor portion being forced to convert the ear interior detected temperature detected by an infrared ray sensor into an electrical signal and to feed it to a display portion, and the body portion interrupts the communication between an external auditory meatus and an outside, the sensor portion is inserted into a ear hole at a suitable position and condition and is formed to be stable in that condition.

Also, in the head blood flow balance inspecting apparatus according to the third aspect of the invention, the connecting portion is a connecting portion made of a U-shaped elastic member elastically surrounding a lower portion of a face or the vicinity thereof, and the electrical signal of the ear interior detected temperature detected by the infrared ray sensor of the sensor portion is fed through the connecting portion to the display portion provided in the midway of the connecting portion.

Also, in the head blood flow balance inspecting apparatus according to the fourth aspect of the invention, the connecting portion is a connecting portion made of a U-shaped elastic member elastically surrounding a lower portion of a face or the vicinity thereof, and the electrical signal of the ear interior detected temperature detected by the infrared ray sensor of the sensor portion is fed through the connecting portion to the display portion provided in the midway of the connecting portion.

Also, in the head blood flow balance inspecting apparatus according to the third aspect of the invention, the connecting portion is a connecting portion made of an elastic member of an inverted U-shaped member fitted around the head portion, and the electrical signal of the ear interior detected temperature detected by the infrared ray sensor of the sensor portion is fed through a transmission cord for feeding the electric signal to the display portion.

Also, in the head blood flow balance inspecting apparatus according to the fourth aspect of the invention, the connecting portion is a connecting portion made of an elastic member of an inverted U-shaped member fitted around the head portion, and the electrical signal of the ear interior detected temperature detected by the infrared ray sensor of the sensor portion is fed through a transmission cord for feeding the electric signal to the display portion.

It is therefore possible to accurately detect the right and left blood flow balance of the head portion by measuring simultaneously the right and left ear hole body temperatures through the two ear interior thermometric portions connected to each other through a connecting portion and displaying the measurement results (the right and left ear interior temperatures or the difference therebetween) on the display portion.

Accordingly, according to the present invention, it is possible to prevent the disease concerning the head portion blood flow, such as the apoplexy or brain infarct, by the right and left blood flow balance of the head portion known exactly.

DESCRIPTION OF THE PREFERRED EMBODIMENTS

Figure 1:
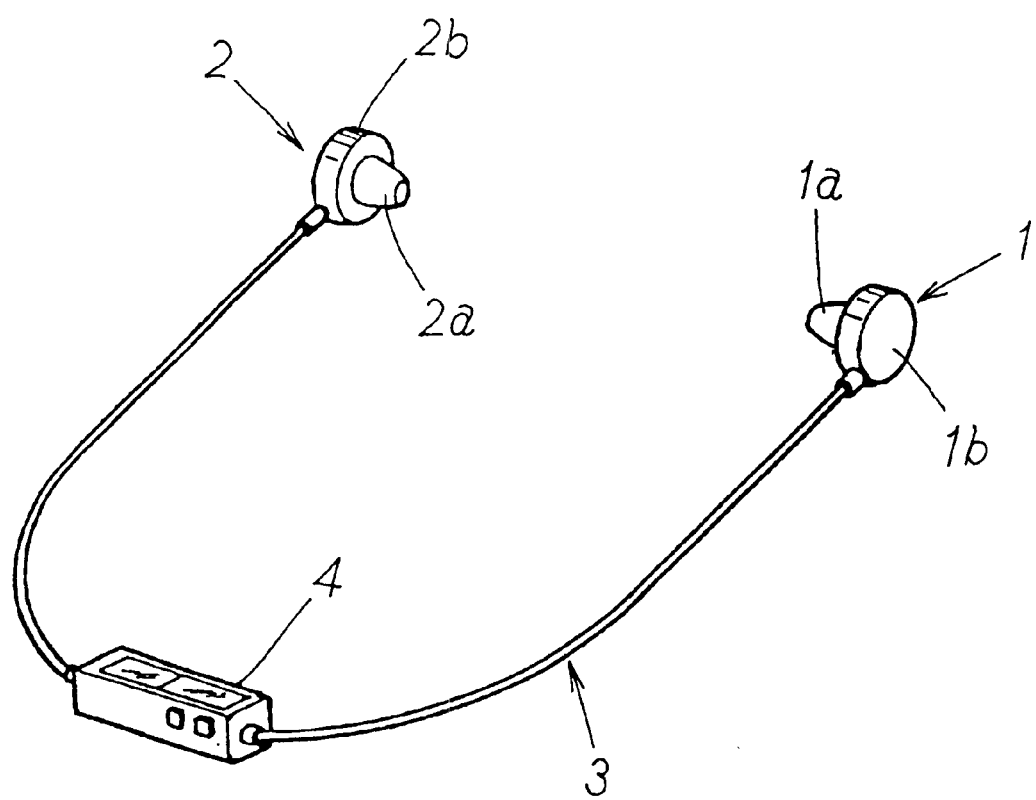
FIG. 1 is a perspective view showing a first embodiment of the invention.
Figure 2:
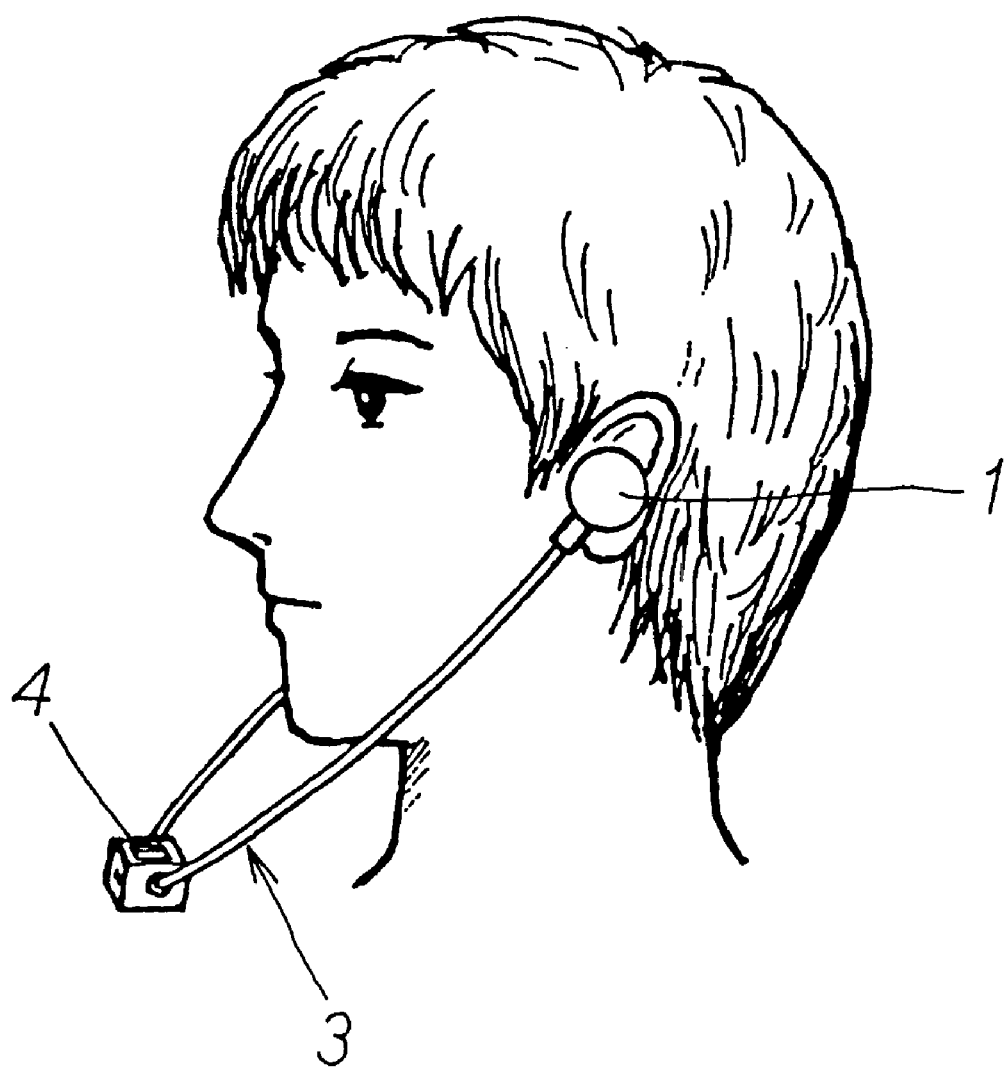
FIG. 2 is an illustration showing a state in which the apparatus according to the first embodiment of the invention is used.

An embodiment of the present invention will now be described with reference to the accompanying drawings. FIGS. 1 and 2 shows a first embodiment in which components are formed in a one-piece manner.

A head blood flow balance inspection apparatus according to the first embodiment is composed of two ear interior thermometric portions 1 and 2, a connecting portion 3 for connecting these two ear interior thermometric portions 1 and 2 and a display portion 4 for displaying a measurement result of the ear interior thermometric portions 1 and 2.

The ear interior thermometric portions 1 and 2 are composed of sensor portions 1a and 2a (probes) to be inserted into the ears and body portions 1b and 2b from which the sensor portions 1a and 2a project, respectively. The sensor portions 1a and 2a contain infrared ray sensors (for detecting infrared ray amount) like a conventional thermometer for measuring the interior of the ear that has been frequently used, respectively, and converting the ear interior detected temperatures into electric signals to feed the signals to the display portion 4 through the connecting portion 3. Also, the body portions 1b and 2b interrupts the communication between external auditory meatuses and the outside and at the same time, have such shapes that the above-described sensor portions 1a and 2a are inserted into the holes of the ears at suitable positions and conditions and those conditions are stabilized.

The connecting portion 3 is formed of elastic material and is provided in the mid way with the display portion 4. The above-described body portions 1b and 2b are connected to the tip end portions of the connecting portion 3. The connecting portion 3 is biased in a direction in which the ear interior thermometric portions 1 and 2 face each other so as not to generate any positional displacement when the above-described sensor portions 1a and 2a are installed within the ears. Also, this connecting portion as a whole is formed into a U-shape to surround the lower portion of the face or the vicinity thereof.

The display portion 4 is used to display the ear interior temperatures (i.e., the infrared ray amounts) detected by the above-described sensor portions 1a and 2a, to display the ear interior temperatures on the right and left sides in parallel, to display the difference of the temperatures, or to alarm the correctness of the difference (in the case where an alarm should occur) by incorporating a judgment circuit therefor.

With such an arrangement according to the first embodiment, the sensor portions 1a and 2a of the above-described ear interior thermometric portions 1 and 2 are inserted into both ears of the person to be inspected, the sensor portions 1a and 2a are held under the suitable positional conditions within both ears by the body portions 1b and 2b, and the ear interior temperatures are measured under the same condition on the right and left sides to display the result on the display 4. As a result, it is possible to know the balance between the right and left blood flows of the head portion and to use the result as material for the countermeasure for preventing the disease concerning the blood flow in the head portion such as apoplexy or brain infarct.

Also, by the biasing effect of the connecting portion 3, it is possible to mount the sensor portions 1a and 2a under the same condition while the mounting angle, the mounting pressure, the mounting depth or the like of the sensor portions 1a and 2a to the ear holes is identified within both ears upon the measurement of the right and left ears. Also in this connection, it is possible to measure the ear interior temperatures in more identified condition.

Figure 3:
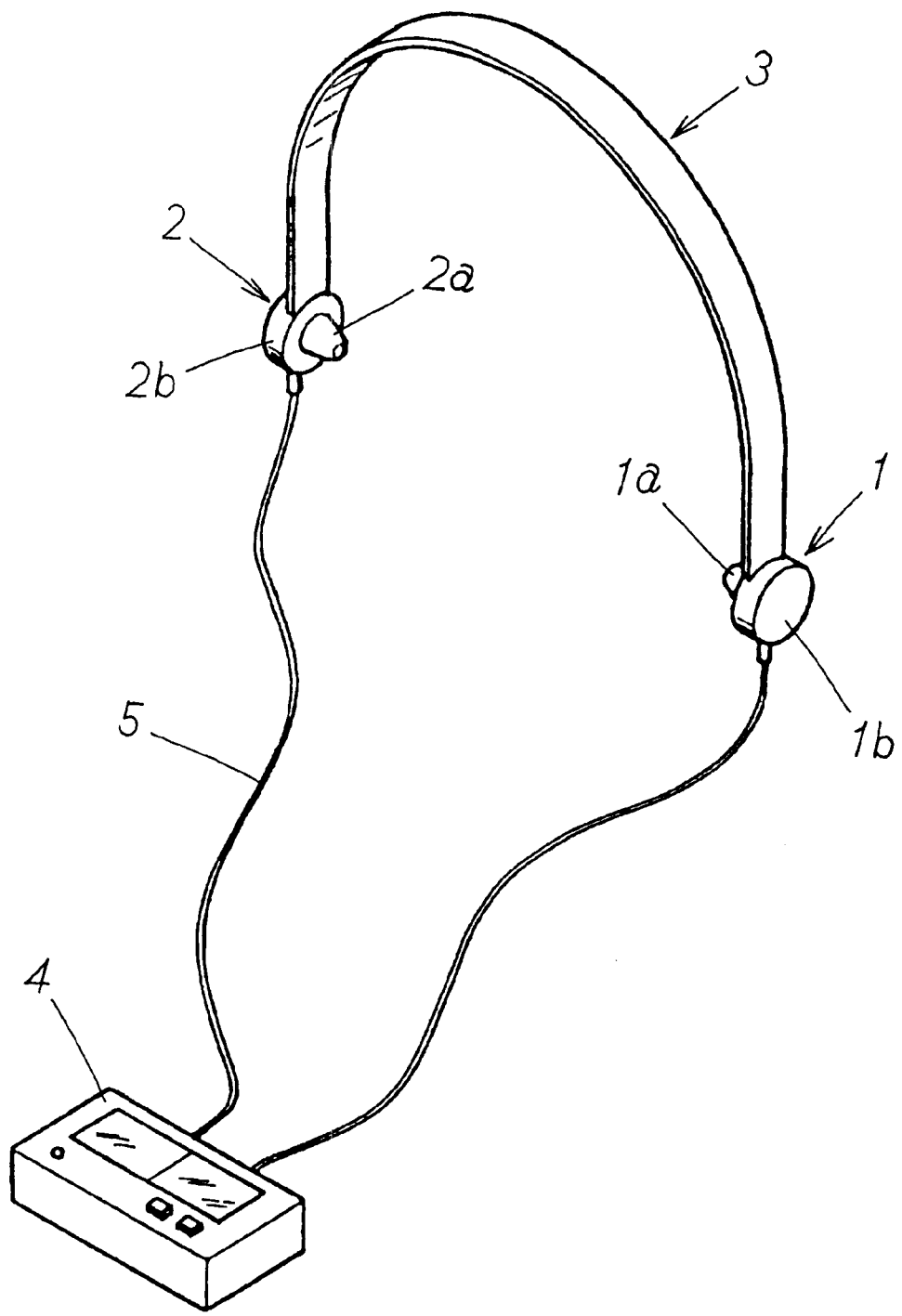
FIG. 3 is a perspective view showing a second embodiment of the invention.

FIG. 3 shows a second embodiment of the present invention in which the connecting portion 3 for connecting the ear interior thermometric portions 1 and 2 is formed into an inverted U-shaped independent member to be fit around the head portion. The electric signals of the ear interior measured temperatures detected by the infrared sensors of the sensor portions 1a and 2a are fed to the display portion 4 through a discrete transmission cord 5 away from the above-described connecting portion 3 for feeding the electric signals.

With such an arrangement according to the second embodiment, the ear interior thermometric portions 1 and 2 are supported by the inverted U-shaped connecting portion 3 to be fitted around the head portion. It is therefore possible to hold the sensor portions 1a and 2a in the suitable positional conditions within both ears in a more stable manner.

Furthermore, since the connecting portion 3 and the display portion 4 are separated from each other, it is possible to enhance the ability of the display portion 4 and readily assemble the judgement circuit or the like for performing the various calculations.

Incidentally, the present invention is not limited to the above-described embodiments. It is sufficient to have the two ear interior thermometric portions, the connecting portion for connecting these two ear interior thermometric portions and the display portion 4 for displaying the measurement result of the above-described two ear interior thermometric portions. Thus, it is possible to take any desired structure for the display means or the temperature measuring means.

The other is the same as that of the first embodiment.

What is claimed is:

1. A method for diagnosing an apoplexy or a brain infarct in a patient, comprising:

inserting an ear-adapted temperature detector into a first ear of the patient;

inserting a different ear-adapted temperature detector into a second ear of the patient;

sensing an internal temperature of each of the first and second ears;

determining a temperature differential between the first and second ears;

displaying either the internal temperatures of each of the first and second ears, or the temperature differential, or both; and diagnosing a presence of the apoplexy or the brain infarct in the patient based, at least in part, upon the temperature differential.

2. The method of claim 1, wherein said sensing an internal temperature of each of the fist and second ears includes sensing an infrared emission.

3. A head blood flow balance inspecting apparatus for diagnosing asymmetric blood flow in a head of a patient, comprising:

two ear interior thermometric portions, said two ear interior thermometric portions each being adapted and arranged about the head of the patient so as to each be insertable into a respective ear of the patient;

a connecting portion for connecting the two ear interior thermometric portions; and a display portion for displaying a measurement result of the two ear interior thermometric portions, wherein a temperature differential between the two ear interior thermometric portions determines, at least in part, whether a blood flow in the head of the patient is asymmetric, wherein said connecting portion connects the two ear interior thermometric portions, the two ear interior thermometric portions being arranged at tip end portions so as to face each other, wherein the connecting portion includes an elastic member which biases the two ear interior thermometric portions in respective directions so as to face each other.

4. The head blood flow balance inspecting apparatus according to claim 3, wherein each of said ear interior thermometric portions includes a sensor portion insertable into a respective ear of the patient, and a body portion projecting with the sensor portion, wherein the sensor portion includes an infrared sensor, said sensor portion converting an ear interior detected temperature detected by the infrared sensor into an electrical signal and feeding said electrical signal to the display portion, wherein the body portion interrupts a communication between an external auditory meatus of the patient and an environment external to the head of the patient, wherein the sensor portion is adapted and arranged to be held in a stable position when inserted into a ear hole of the respective ear of the patient.

5. The head blood flow balance inspecting apparatus according to claim 4, wherein the connecting portion is an elastic, inverted U-shaped member arranged so as to be fittable around a head portion of the patient, wherein the electrical signal is fed through a transmission cord which couples the electric signal to the display portion.

6. The head blood flow balance inspecting apparatus according to claim 4, wherein the connecting portion includes a U-shaped elastic member elastically surrounding a lower portion of a face of the patient or in a vicinity thereof, wherein the electrical signal is fed through the connecting portion to the display portion, wherein the display portion is arranged at a point essentially midway between the two ear interior thermometric portions on the connecting portion.

7. A head blood flow balance inspecting apparatus for diagnosing asymmetric blood flow in a head of a patient, comprising:

two ear interior thermometric portions, said two ear interior thermometric portions each being adapted and arranged about the head of the patient so as to each be insertable into a respective ear of the patient;

a connecting portion for connecting the two ear interior thermometric portions; and a display portion for displaying a measurement result of the two ear interior thermometric portions, wherein a temperature differential between the two ear interior thermometric portions determines, at least in part, whether a blood flow in the head of the patient is asymmetric, wherein each of said ear interior thermometric portions includes a sensor portion insertable into a respective ear of the patient, and a body portion projecting with the sensor portion, wherein the sensor portion includes an infrared sensor, said sensor portion converting an ear interior detected temperature detected by the infrared sensor into an electrical signal and feeding said electrical signal to the display portion, wherein the body portion interrupts a communication between an external auditory meatus of the patient and an environment external to the head of the patient, wherein the sensor portion is adapted and arranged to be held in a stable position when inserted into a ear hole of the respective ear of the patient.

8. The head blood flow balance inspecting apparatus according to claim 7, wherein the connecting portion includes a U-shaped elastic member elastically surrounding a lower portion of a face of the patient or in a vicinity thereof, wherein the electrical signal is fed through the connecting portion to the display portion, wherein the display portion is arranged at a point essentially midway between the two ear interior thermometric portions on the connecting portion.

9. The head blood flow balance inspecting apparatus according to claim 7, wherein the connecting portion is an elastic, inverted U-shaped member arranged so as to be fittable around a head portion of the patient, wherein the electrical signal is fed through a transmission cord which couples the electric signal to the display portion.

10. A device for diagnosing apoplexy or a brain infarct in a patient, comprising:

a pair of ear probes, each of said ear probes being adapted so as to be insertable into a respective ear of the patient and to block communication between an interior portion of the respective ear and an external environment;

two temperature detectors, each of said two temperature detectors being arranged within an associated ear probe to measure an internal temperature of the respective ear; and a display section coupled to said two temperature detectors, said display section at least displaying a temperature differential between said two temperature detectors, wherein a diagnosis of either an apoplectic condition or a brain infarction is determined, at least in part, based upon the temperature differential, wherein said two temperature detectors are two infrared-type temperature detectors.

* * * * *

UNITED STATES PATENT AND TRADEMARK OFFICE
CERTIFICATE OF CORRECTION

PATENT NO. : 6,511,437 B1
DATED : January 28, 2003
INVENTOR(S) : Yoshinobu Nakamura et al.

It is certified that error appears in the above-identified patent and that said Letters Patent is hereby corrected as shown below:

Column 1,
Line 17, replace the word "unbalance" with the word -- unbalanced --.
Line 18, replace the word "is" with the word -- are --.
Line 22 replace the word "know" with the word -- determine --.
Line 22, delete the second occurrence of the word "the".
Line 23, delete the word "means".
Line 23, replace the word "on" with the word -- in --.
Line 24, delete the third (last) occurrence of the word "the".
Line 26, delete the phrase "is provided".
Line 26, replace the word "with" with the word -- has --.
Line 27, delete the phrase "in the case".
Line 28, replace the words "in order" with the word -- sequentially --.
Line 29, replace line 29 with -- equipment. Therefore the ear interior temperatures on the right and left. --.
Line 31, replace the word "condition" with the word -- conditions, --.
Line 31, insert the phrase -- , for example, -- after the word "to".
Line 32, delete the phrase "to be measured by".
Line 32, delete the words "by the".
Line 33, delete the word "person".
Line 33, delete the word "the".
Line 38, insert the word -- to -- after the word "is".
Line 41, delete the word "there".
Line 42, delete the words "is provided".
Line 43, replace the word "comprising" with the phrase -- is provided which comprises --.

Column 2,
Line 11, insert a -- comma (,) -- after the word "condition".
Line 49, replace the words "ear hole" with the word -- ear-hole --.
Line 51, insert a -- comma (,) -- after the word a "portion".
Line 56, replace the phrase "prevent the disease concerning the" with the phrase -- detect disease relating to asymmetric --.
Line 57, delete first occurrence of the word "the".
Line 57, insert the word -- a --after the word "or".
Line 57, insert the words -- "exactly determining -- after the word "by".
Line 58, replace the phrase "head portion known" with -- head portion --.
Line 59, delete the word "exactly".

UNITED STATES PATENT AND TRADEMARK OFFICE
CERTIFICATE OF CORRECTION

PATENT NO. : 6,511,437 B1
DATED : January 28, 2003
INVENTOR(S) : Yoshinobu Nakamura et al.

It is certified that error appears in the above-identified patent and that said Letters Patent is hereby corrected as shown below:

<u>Column 3,</u>
Line 11, replace the phrase "is composed of" with the word -- includes --
Line 21, replace the word "amount" with the word -- emission --.
Line 22, delete the phrase "has been frequently".
Line 23, replace the word "used" with the words -- is known --.
Line 33, replace the phrase "in the mid way with" with the words -- at an approximate mid-way position with --.
Line 37, insert a -- comma (,) -- after the word "other".
Line 44, insert the word -- detected -- after first occurrence of the word "the".
Line 44, replace the word "amounts" with the word -- emissions --.
Line 46, replace the words "in parallel" with the word -- simultaneously --.
Line 47, insert the words -- "provide an" -- after the second occurrence of the word "to".
Line 48, replace the word "the" with the words -- regarding the --.
Line 48, insert the word -- temperature -- after first occurrence of the word "the".
Line 49, delete the word "therefor".
Line 57, insert the word --simultaneously -- before the word "under".
Lines 60 and 62, insert a -- comma (,) -- after the word "portion".
Line 60, replace the words "material for the" with the words -- a diagnostic tool --.
Line 61, delete the word "countermeasure".
Line 62, insert the word -- a -- after the word "or".
Line 66, insert a -- comma (,) -- after the word "condition".

UNITED STATES PATENT AND TRADEMARK OFFICE
CERTIFICATE OF CORRECTION

PATENT NO. : 6,511,437 B1
DATED : January 28, 2003
INVENTOR(S) : Yoshinobu Nakamura et al.

It is certified that error appears in the above-identified patent and that said Letters Patent is hereby corrected as shown below:

Column 4,
Line 4, insert the word -- repeatedly -- after the word "to".
Line 5, delete the phrase "more identified condition" and replace it with the phrase -- relatively the same position --.
Line 9, delete the word "be".
Line 12, insert -- ; and -- after the word "2a".
Lines 14-15, delete the phrase "for feeding the electric signals".
Line 19, replace the words "to be" with the words -- which is --.
Line 20, delete second occurrence of the word "the".
Line 25, insert a -- comma (,) -- after the number "4".
Line 25, insert the word -- to -- after the word "and".
Line 26, replace the misspelled word "judgement" with the word -- judgment --.
Line 37, delete the entire line 37.

Signed and Sealed this

Thirteenth Day of April, 2004

JON W. DUDAS
*Acting Director of the United States Patent and Trademark Office*